US010112000B2

(12) United States Patent
Kitaguchi et al.

(10) Patent No.: US 10,112,000 B2
(45) Date of Patent: Oct. 30, 2018

(54) METHOD FOR REDUCING AMYLOID BETA CONCENTRATION IN BLOOD

(75) Inventors: Nobuya Kitaguchi, Toyoake (JP); Kazunori Kawaguchi, Toyoake (JP)

(73) Assignees: ASAHI KASEI MEDICAL CO., LTD., Tokyo (JP); SCHOOL JURIDICAL PERSON FUJITA EDUCATIONAL INSTITUTION, Aichi (JP)

(*) Notice: Subject to any disclaimer, the term of this patent is extended or adjusted under 35 U.S.C. 154(b) by 344 days.

(21) Appl. No.: 13/178,790

(22) Filed: Jul. 8, 2011

(65) Prior Publication Data
US 2012/0031840 A1  Feb. 9, 2012

Related U.S. Application Data

(60) Provisional application No. 61/344,376, filed on Jul. 8, 2010.

(51) Int. Cl.
| B01D 71/68 | (2006.01) |
| B01D 69/08 | (2006.01) |
| B01D 71/26 | (2006.01) |
| B01D 71/16 | (2006.01) |
| B01D 71/42 | (2006.01) |
| B01D 71/10 | (2006.01) |
| B01D 61/24 | (2006.01) |
| B01D 71/40 | (2006.01) |
| A61M 1/36 | (2006.01) |
| B01D 63/02 | (2006.01) |
| B01D 71/44 | (2006.01) |

(52) U.S. Cl.
CPC ........... *A61M 1/3679* (2013.01); *B01D 63/02* (2013.01); *B01D 71/10* (2013.01); *B01D 71/16* (2013.01); *B01D 71/40* (2013.01); *B01D 71/44* (2013.01); *B01D 71/68* (2013.01)

(58) Field of Classification Search
CPC ..... A61M 1/3679; B01D 63/02; B01D 71/10; B01D 71/16; B01D 71/40; B01D 71/44; B01D 71/68
See application file for complete search history.

(56) References Cited

U.S. PATENT DOCUMENTS

| 4,445,885 | A | * | 5/1984 | Kifune | ................ | A61M 1/3427 210/500.23 |
| 5,260,224 | A | | 11/1993 | Stossel et al. | | |
| 5,407,581 | A | * | 4/1995 | Onodera | ............ | B01D 39/1623 210/321.69 |
| 7,851,446 | B2 | | 12/2010 | Roura | | |
| 2006/0045853 | A1 | | 3/2006 | Kroon-Batenburg et al. | | |
| 2006/0129082 | A1 | * | 6/2006 | Rozga | ................. | A61M 1/3472 604/6.04 |
| 2007/0007193 | A1 | | 1/2007 | Uchi et al. | | |
| 2007/0010435 | A1 | * | 1/2007 | Frangione et al. | ............. | 514/12 |
| 2007/0080108 | A1 | * | 4/2007 | Kuroda | .............. | B01D 67/0011 210/500.23 |
| 2007/0082401 | A1 | | 4/2007 | Wada et al. | | |
| 2007/0251882 | A1 | * | 11/2007 | Bradwell et al. | ............. | 210/646 |
| 2008/0051690 | A1 | | 2/2008 | Mattner et al. | | |
| 2008/0237127 | A1 | | 10/2008 | Okafuji et al. | | |
| 2009/0111740 | A1 | | 4/2009 | Grifols Roura | | |
| 2011/0274594 | A1 | | 11/2011 | Kitaguchi et al. | | |

FOREIGN PATENT DOCUMENTS

| CA | 1324470 C | 10/1988 |
| JP | H01-115364 A | 5/1989 |
| JP | 2003-265601 A | 9/2003 |
| JP | 2004-216143 A | 8/2004 |
| JP | 2005-237755 A | 9/2005 |
| JP | 2005-537254 | 12/2005 |
| JP | 2005-52716 | 9/2006 |
| JP | 2007-215992 A | 8/2007 |
| JP | 2008-506665 | 3/2008 |
| JP | 2009-108059 | 5/2009 |
| JP | 2009-297229 A | 12/2009 |
| WO | 1991/015770 | 10/1991 |
| WO | 2004/094047 | 11/2004 |
| WO | 2005/028500 A1 | 3/2005 |
| WO | 2006/024902 | 3/2006 |
| WO | 2010/073580 | 7/2010 |

OTHER PUBLICATIONS

Kuo et al., "Water-soluble Aβ (N-40, N-42) Oligomers in Normal and Alzheimer Disease Brains", The Journal of Biological Chemistry, 1996, pp. 4077-4081.
Selkoe, "Alzheimer's Disease: Genes, Proteins, and Therapy", Physiological Reviews, 2001, pp. 741-766.
Hung et al., "Amyloid-β Peptide (AB) Neurotoxicity Is Modulated by the Rate of Peptide Aggregation: Aβ Dimers and Trimers Correlate With Neurotoxicity", The Journal of Neuroscience, 2008, pp. 11950-11958.
Schenk et al., "Immunization with amyloid-β attenuates Alzheimer-disease-like pathology in the PDAPP mouse", Nature, 1999, pp. 173-177.
Hock et al., "Antibodies against β-Amyloid Slow Cognitive Decline in Alzheimer's Disease", Neuron, 2003, pp. 547-554.
Demattos et al., "Peripheral anti-Aβ antibody alters CNS and plasma Aβ clearance and decreases brain Aβ burden in a mouse model of Alzheimer's disease", 2001, PNAS, pp. 8850-8855.
Donahue et al., "RAGE, LRP-1, and amyloid-beta protein in Alzheimer's disease", Acta Neuropathol , 2006, pp. 405-415.

(Continued)

*Primary Examiner* — Dirk R Bass
(74) *Attorney, Agent, or Firm* — Greenblum & Bernstein P.L.C.

(57) ABSTRACT

The present invention relates to a method for reducing a β-amyloid concentration in blood. Specifically, the present invention relates to a method for reducing a β-amyloid concentration in blood, comprising the steps of; removing blood out of a body, passing the blood that is removed through a hollow fiber membrane, and returning the blood that is passed through into the body, wherein the blood containing a β-amyloid-albumin complex is passed through the hollow fiber membrane to allow β-amyloid to adsorb to the hollow fiber membrane so that the β-amyloid concentration in blood is reduced.

25 Claims, No Drawings

(56) References Cited

OTHER PUBLICATIONS

Bell et al., "Transport pathways for clearance of human Alzheimer's amyloid β-peptide and apolipoproteins E and J in the mouse central nervous system", Journal of Cerebral Blood Flow & Metabolism, 2007, pp. 909-918.
Silverberg et al., "Amyloid Deposition and Influx Transporter Expression at the Blood-Brain Barrier Increase in Normal Aging", J Neuropathol Exp Neurol, 2010, pp. 98-108.
Kawaguchi et al., "Novel therapeutic approach for Alzheimer's disease by removing amyloid β protein from the brain with an extracorporeal removal system", J Artif Organs, 2010, pp. 31-37.
Schoonenboom et al., "Amyloid β 38, 40, and 42 Species in Cerebrospinal Fluid: More of the Same?", American Neurological Association, 2005, pp. 139-142.
Lopez et al., "Plasma amyloid levels and the risk of AD in normal subjects in the Cardiovascular Health Study", Neurology, 2008, pp. 1664-1671.
Hasegawa, "Kinetic Modeli9ng and Determination of Reaction Constants of Alzheimer's β-Amyloid Fibril Extension and Dissociation Using Surface Plasmon Resonance", Biochemistry, 2002, pp. 13489-13498.
Holsinger et al., "Does This Patient Have Dementia?", JAMA, 2007, pp. 2391-2404.
Bateman, "Amyloid-Beta Production and Clearance Rates in Alzheimer's Disease", ICAD, 2010, PP.
Kitaguchi et al., "Reduction of Alzheimer's Disease Amyloid-β in Plasma by Hemodialysis and Its Relation to Cognitive Functions", Blood Purification, 2011, pp. 57-62.
Bayer et al., "Evaluation of the safety and immunogenicity of synthetic Aβ 42 (AN1792) in patients with AD", Neurology, 2005, pp. 94-101.
Bergamaschini et al., "Peripheral Treatment with Enoxaparin, a Low Molecular Weight Heparin, Reduces Plaques and β-Amyloid Accumulation in a Mouse Model of Alzheimer's Disease", The Journal of Neuroscience, 2004, pp. 4181-4186.
Kawaguchi et al., "Toward the Novel Method of Treatment for Alzheimer's Disease: Extra-Corporeal Aβ Removal System (EARS)", Alzheimer's & Dementia, 2009, pp. P3-244.
Liu et al., "Expression of Neprilysin in Skeletal Muscle Reduces Amyloid Burden in a Transgenic Mouse Model of Alzheimer Disease", Molecular Therapy, 2009, pp. 1381-1386.
Boada et al., "Amyloid-Targeted Therapeutics in Alzheimer's Disease: Use of Human Albumin in Plasma Exchange as a Novel Approach for Aβ Mobilization", Drug News Perspect, 2009, pp. 325-339.
Bateman et al., "Human amyloid-β synthesis and clearance rates as measured in cerebrospinal fluid in vivo", Nature Medicine, 2006, pp. 856-861.
Mawuenyega et al., "Decreased Clearance of CNS β-Amyloid in Alzheimer's Disease", Science, 2010, pp. 1774.
Boada-Rovira, "Human Albumin Grifols® 5% in plasmapheresis: a new therapy involving beta-amyloid mobilisation in Alzheimer's disease", Rev Neurol (English Abstract), 2010, pp. S9-S18.
Sadahiro et al., "The Efficacy and Mechanism of Cytokine Removal with Continuous Hemodiafiltration during Critical Care", Japanese Journal of Apheresis (English Abstract), 1999, pp. 41-47.
Kitaguchi et al., "Toward therapeutic system for Alzheimer's Disease by removal of blood Aβ: Hemodialysis improved the impaired cognitive states of renal failure patients",,, PP.

Levites et al., "Intracranial Adeno-Associated Virus-Mediated Delivery of Anti-Pan Amyloid β, Amyloid β40, and Amyloid β42 Single-Chain Variable Fragments Attenuates Plaque Pathology in Amyloid Precursor Protein Mice", The Journal of Neuroscience, 2006, pp. 11923-11928.
Kitaguchi et al., "Therapeutic System for Alzheimer's Disease by Blood Purification with Extra-Corporeal Aβ Removal System (EARS): Reduction of Plasma Aβ by Hemodialysis", Alzheimer's & Dimentia, 2010, pp. P3-312.
Holmes et al., "Long-term effects of Aβsub 42 immunisation in Alzheimer's disease: follow-up of a randomised, placebo-controlled phase I trial", Lancet, 2008, pp. 216-233.
Lemere et al., "Evidence for peripheral clearance of cerebral Aβ protein following chronic, active Aβ immunization in PSAPP mice", Neurobiology of Disease, 2003, pp. 10-18.
Matsuoka et al., "Novel Therapeutic Approach for the Treatment of Alzheimer's Disease by Peripheral Administration of Agents with an Affinity to β-Amyloid", The Journal of Neuroscience, 2003, pp. 29-33.
Rubio et al., "Plasma amyloid-β, Aβsub1-42, load is reduced by haemodialysis", Journal of Alzheimer's Disease, 2006, pp. 439-443.
Alzheimer's Association International Conference 2011, Daily Program, Monday Jul. 18, p. 2-469.
Japanese Society of Neurology, Clinical Neurology, 2011, vol. 51, May 20, 2011, pp. 3-165.
Alzheimer's Association 2009 International Conference on Alzheimer's Disease (ICAD), Daily Program, Tuesday Jul. 14, 2009, pp. 37.
Motomura et al., Kidney and dialysis, Supplementary, Investigation into the Paradox of HPM (III), Clinical Studies.
Motomura et al., Kidney and dialysis, Supplementary volume, Investigation into the Paradox of HPM (I), Clinical Studies.
Kazunori Kawaguchi et al., "Towards Construction of Alzheimer's Disease Treatment System based on Blood Purification", vol. 22.
Kazunori Kawaguchi et al., "Towards Construction of Alzheimer's Disease Treatment System based on Blood Amyloid β Protein (Aβ) Removal—Adsorption properties of Aβ Adsorbents", Japanese Society, vol. 23.
Alzheimer's Association, International Conference on Alzheimer's Disease 2010, Daily Program, Tuesday, Jul. 13, 2010, p. 3-312 (p. 44).
Shingo Takesawa et al., "High Performance Dialyzer 2008", Tokyo Igakusha Co., Ltd., First edition issued on Jul. 15, 2008, p. 49-59.
Unknown, "Guidelines for Maintenance Hemodialysis: Hemodialysis Prescriptions," Journal of Japanese Society for Dialysis Therapy, 2013, 46(7):589-590 with partial English translation.
Tomisawa et al., "Amount of adsorbed albumin loss by dialysis membranes with protein adsorption," J Artif Organs (2009) 12:194-199.
Unknown, "Blood Purifiers: Basics of Performance Evaluation," Kidney and Dialysis, 2007, 63:8-11, with partial English translation.
Tateishi et al., "Continuous hemodiafiltration in the treatment of reactive hemophagocytic syndrome refractory to medical therapy," Transfusion and Apheresis Science (2009), 40:33-40.
Unknown, "Guideline for newborn acute blood purification therapy by extracorporeal circulation," Journal of Japan Society for Premature and Newborn Medicine, 2013, 25(1):89-97, with partial English translation.
Blood purification therapy handbook, 2010, pp. 23-25 and 75-77, with partial English translation.
Toray Hemofeel(Trademark)CH product catalog, 2007, with partial English translation.

* cited by examiner

METHOD FOR REDUCING AMYLOID BETA CONCENTRATION IN BLOOD

CROSS-REFERENCE TO RELATED APPLICATION

The present application is based on U.S. Provisional Patent Application No. 61/344,376 filed on Jul. 8, 2010. The contents of this U.S. Provisional Patent Application, literatures cited therein, and literatures described in the specification of the present application are incorporated herein by reference.

TECHNICAL FIELD

The present invention relates to a method for reducing a β-amyloid concentration in blood.

BACKGROUND ART

Alzheimer's disease (AD) is a disease in which the degeneration of nerve cells in the brain is thought to lead to dementia. The most plausible hypothesis for the pathogenic mechanism of Alzheimer's disease is "amyloid hypothesis", which proposes that the accumulation of β-amyloid (hereinafter, sometimes abbreviated as "Aβ") in the brain is the beginning of the disease. It is considered that soluble Aβ strongly inhibits long-term potentiation of memory, and deposits of aggregated Aβ form fibril, thereby leading to neuronal cell death.

Non-patent document 1 discloses that administration of anti-Aβ antibodies, that is an antibody against Aβ, and Aβ vaccines leads to not only improvement in the symptoms of dementia but also disappearance of Aβ deposition in the brain, suggesting the possibility of cure for Alzheimer's disease.

However, while the development of anti-Aβ antibodies with excellent therapeutic effect has been advanced by a large number of research groups, treatment with the anti-Aβ antibody places a great burden on patients since it is expensive and takes long time. Also, there is another problem that owing to a relatively short efficacy of anti-Aβ antibody treatment, repetitive administration becomes necessary.

Further, as evidenced by such an incident that a clinical trial was discontinued due to death caused by an adverse reaction of Aβ vaccine administration (Non-patent document 2), there is still a long way to the establishment of therapy for Alzheimer's disease.

Experiments using mouse models of Alzheimer's disease show that the amount of Aβ in blood significantly increases as the brain Aβ decreases (Non-patent document 3), peripheral administration of non-immunostimulatory Aβ-binding substances (i.e., gelsolin and GM1 ganglioside) reduces the amount of Aβ in the brain (Non-patent documents 4 and 5), administration of non-immunostimulatory anti-Aβ antibody Fab fragments via the blood reduces the amount of Aβ in the brain (Non-patent document 6), and so on, from which the "sink hypothesis", meaning that the efflux of Aβ from the brain into the blood occurs as the amount of Aβ in blood decreases, is proposed. Also, in relation with this hypothesis, Non-patent documents 7 and 8 disclose that the amount of Aβ in blood is reduced by artificial dialysis.

Further, patent documents 1-3 disclose technology relating to an Aβ remover, which removes Aβ in blood by extracorporeal circulation of the blood.

PRIOR ART DOCUMENT

Patent Document

[Patent Document 1] PCT International Publication WO 2010/073580 Pamphlet
[Patent Document 2] Japanese Translation of PCT International Application Publication JP 2005-537254
[Patent Document 3] Japanese Translation of PCT International Application Publication JP 2008-506665

Non-Patent Document

[Non-patent Document 1] Bayer, A. et al., Neurology, 2005, 64, pages 94 to 101
[Non-patent Document 2] Holmes, C. et al., Lancet, 2008, 372 (9634), pages 216 to 223
[Non-patent Document 3] Lemere, C. A. et al., Nuerobiol. Dis., 2003, 14, pages 10 to 18
[Non-patent Document 4] Matsuoka, Y. et al., J. Neurosci., 2003, 23, pages 29 to 33
[Non-patent Document 5] Bergamaschini, L. et al., J. Neurosci., 2004, 24, pages 4148 to 4186
[Non-patent Document 6] Levites, Y. et al., J. Neurosci., 2006, 26, pages 11923 to 11928
[Non-patent Document 7] The Journal of the Kyoto Medical Association, Vol. 53, No. 1, June 2006, pages 113 to 120
[Non-patent Document 8] Isabel, R. et al., Journal of Alzheimer's Disease, 2006, 10, pages 439 to 443

DISCLOSURE OF INVENTION

Problem to be Solved by the Invention

In view of the "sink" hypothesis, the present inventors considered that efficient removal of Aβ in blood of AD patients would serve as efficient means of treatment or prevention of Alzheimer's disease.

In light of the above, the present invention aims to provide a method capable of efficiently removing Aβ in blood and a system thereof.

Means for Solving the Problem

As a result of diligent research aimed at solving the aforementioned problems, the present inventors have found that the β-amyloid concentration in blood is reduced and Aβ in blood is efficiently removed by adsorption of Aβ to a hollow fiber membrane, thereby completing the present invention.

That is, the present invention provides the following method for reducing a β-amyloid concentration in blood and a system thereof.

A method for reducing a β-amyloid concentration in blood, comprising the steps of;
 removing blood out of a body,
 passing the blood that is removed through a hollow fiber membrane, and
 returning the blood that is passed through into the body, wherein the blood containing a β-amyloid-albumin complex is passed through the hollow fiber membrane to allow β-amyloid to adsorb to the hollow fiber membrane so that the β-amyloid concentration in blood is reduced.

The method according to [1], wherein β-amyloid from the β-amyloid-albumin complex adsorbs to the hollow fiber membrane and albumin from the β-amyloid-albumin complex is liberated into the blood.

The method according to [1], wherein a flow rate of the blood is 5 to 200 mL/min.

The method according to [1], wherein a flow rate of the blood is 10 to 30 mL/min.

The method according to [1], wherein the blood is passed through an inner cavity of the hollow fiber.

The method according to [1], wherein a linear velocity of the blood in the inner cavity of the hollow fiber is 200 cm/min or less.

The method according to [1], wherein a linear velocity of the blood in the inner cavity of the hollow fiber is 5 cm/min or less.

The method according to [1], wherein gas or liquid is present at an outer surface of the hollow fiber.

The method according to [1], wherein a dialysate is passed through an outer surface of the hollow fiber.

The method according to [9], wherein a β-amyloid concentration in the dialysate is substantially not increased.

The method according to [1], wherein the blood is passed through an outer surface of the hollow fiber.

The method according to [11], wherein gas or liquid is present in an inner cavity of the hollow fiber.

The method according to [1], wherein the hollow fiber membrane comprises a polymer selected from the group consisting of polysulfone (PSf), polymethylmethacrylate (PMMA), polyethersulfone-polyarylate polymer alloy (PEPA), polyethersulfone (PES), polyacrylonitrile (PAN), cellulose triacetate (CTA), modified cellulose (BEM), and an ethylene vinyl alcohol copolymer (EVAL).

The method according to [11], wherein the hollow fiber membrane further comprises polyvinylpyrrolidone.

The method according to [1], wherein the hollow fiber membrane is inserted in a housing having an inlet port and an outlet port for the blood.

The method according to [13], wherein the hollow fiber membrane is inserted in a housing and sealed at an inlet port and an outlet port.

The method according to [14], wherein a housing inserting a hollow fiber membrane is a hemodialysis column.

The method according to [13], wherein a fragment of the hollow fiber membrane is inserted in a housing.

A method for reducing a β-amyloid concentration in blood to treat or prevent Alzheimer's disease, comprising the steps of;

removing blood out of a body of a patient with Alzheimer's disease, passing the blood that is removed through a hollow fiber membrane, and returning the blood that is passed through into the body of the patient, wherein the blood containing a β-amyloid-albumin complex is passed through the hollow fiber membrane to allow β-amyloid to adsorb to the hollow fiber membrane so that β-amyloid concentration in blood is reduced.

The method according to [1], wherein a linear velocity of the blood at the outer surface of the hollow fiber corresponds to 200 cm/min or less.

The method according to [1], wherein a linear velocity of the blood at the outer surface of the hollow fiber corresponds to 5 cm/min or less.

The present invention also provides the following β-amyloid removal system.

A β-amyloid removal system comprising;

a hollow fiber membrane that adsorbs β-amyloid and reduces a β-amyloid concentration in blood, a blood circuit that removes blood out of a body, a blood circuit that returns the blood that is passed through the hollow fiber membrane, and flexible tubes connecting the blood circuits to the hollow fiber membrane.

The β-amyloid removal system according to [22], wherein β-amyloid from the β-amyloid-albumin complex adsorbs to the hollow fiber membrane and albumin from the β-amyloid-albumin complex is liberated into the blood.

The β-amyloid removal system according to [22] or [23], wherein a flow rate of the blood is 5 to 200 mL/min.

The β-amyloid removal system according to any of [22] to [24], wherein a flow rate of the blood is 10 to 30 mL/min.

The β-amyloid removal system according to any of [22] to [25], wherein the blood is passed through an inner cavity of the hollow fiber.

The β-amyloid removal system according to any of [22] to [26], wherein a linear velocity of the blood in the inner cavity of the hollow fiber is 200 cm/min or less.

The β-amyloid removal system according to any of [22] to [27], wherein a linear velocity of the blood in the inner cavity of the hollow fiber is 5 cm/min or less.

The β-amyloid removal system according to any of [22] to [28], wherein gas or liquid is present at an outer surface of the hollow fiber.

The β-amyloid removal system according to any of [22] to [29], wherein a dialysate is passed through the outer surface of the hollow fiber.

The β-amyloid removal system according to [30], wherein a β-amyloid concentration in the dialysate is substantially not increased.

The β-amyloid removal system according to any of [22] to [25], wherein the blood is passed through the outer surface of the hollow fiber.

The β-amyloid removal system according to [32], wherein gas or liquid is present in an inner cavity of the hollow fiber.

The β-amyloid removal system according to any of [22] to [33], wherein the hollow fiber membrane comprises a polymer selected from the group consisting of polysulfone (PSf), polymethylmethacrylate (PMMA), polyethersulfone-polyarylate polymer alloy (PEPA), polyethersulfone (PES), polyacrylonitrile (PAN), cellulose triacetate (CTA), modified cellulose (BEM), and an ethylene vinyl alcohol copolymer (EVAL).

The β-amyloid removal system according to [34], wherein the hollow fiber membrane further comprises polyvinylpyrrolidone.

The β-amyloid removal system according to any of [22] to [35], wherein the hollow fiber membrane is inserted in a housing having an inlet port and an outlet port for the blood.

The β-amyloid removal system according to [36], wherein the hollow fiber membrane is inserted in the housing and sealed at the inlet port and the outlet port.

The β-amyloid removal system according to [36] or [37], wherein the housing inserting the hollow fiber membrane is a hemodialysis column.

The β-amyloid removal system according to [36], wherein a fragment of the hollow fiber membrane is inserted in the housing.

The β-amyloid removal system according to any of [22] to [25] and [32] to [39], wherein a linear velocity of the blood at the outer surface of the hollow fiber corresponds to 200 cm/min or less.

The β-amyloid removal system according to any of [22] to [25] and [32] to [40], wherein a linear velocity of the blood at the outer surface of the hollow fiber corresponds to 5 cm/min or less.

Advantageous Effect of the Invention

The present invention can provide a method capable of efficiently removing the amount of Aβ in blood and a system thereof.

MODE FOR CARRYING OUT THE INVENTION

Hereinbelow, embodiments of the present invention (hereinafter, referred to as "the present embodiment") will be described in detail. It is to be noted that the present invention is not limited to the following embodiments but can be practiced in various modified forms within the scope of the main idea of the present invention.

The method for reducing a β-amyloid concentration in blood according to the present embodiment comprises the steps of;
removing blood out of a body,
passing the blood that is removed through a hollow fiber membrane, and
returning the blood that is passed through into the body,
wherein the blood containing a β-amyloid-albumin complex is passed through the hollow fiber membrane to allow β-amyloid to adsorb to the hollow fiber membrane so that β-amyloid concentration in blood is reduced.

The method for reducing the β-amyloid concentration in blood can be performed by extracorporeal circulation, which includes removing the blood out of a body, passing the blood thus removed through a hollow fiber membrane, and returning the blood thus passed through into the body.

While a series of the above steps can be performed as a similar method to blood purification technique such as so-called artificial dialysis and blood filtration, as one example, a blood circuit composed of flexible tubes is used so as to extracorporeally circulate a patient's blood.

A blood circuit for extracorporeal circulation generally comprises an arterial blood circuit having an arterial side puncture needle on its tip to draw blood from a patient, a venous blood circuit having a venous side puncture needle on its tip to return the blood to the patient, and a hollow fiber membrane between the arterial blood circuit and the venous blood circuit.

The arterial blood circuit, the hollow fiber membrane, and the venous blood circuit are connected via flexible tubes, and the blood that is removed from a patient is brought into contact with the hollow fiber membrane via the flexible tubes.

That is, the blood is removed from inside to outside the body of a patient via the arterial blood circuit and then introduced into the blood circuit. The blood then flows through the flexible tubes in the blood circuit to the hollow fiber membrane.

The β-amyloid-albumin complex in blood flowing through the hollow fiber membrane contacts the hollow fiber membrane, whereby β-amyloid adsorbs to the hollow fiber membrane and thus the β-amyloid concentration in blood after having passed through the hollow fiber membrane is reduced. Further, β-amyloid that is not bound to albumin is also removed by adsorption to the hollow fiber membrane.

The blood that is discharged from the hollow fiber membrane after having passed through the hollow fiber membrane is returned from the outside to the inside of the patient body via the venous blood circuit as blood having a reduced blood β-amyloid concentration.

The method for reducing a β-amyloid concentration in blood according to the present embodiment can be applied to a patient with Alzheimer's disease, whereby it can reduce the β-amyloid concentration in blood of the patient with Alzheimer's disease.

There is no particular limitation on the patient with Alzheimer's disease as long as the patient can be subjected to extracorporeal circulation. Also, the method for reducing a β-amyloid concentration in blood according to the present embodiment can be applied to a patient who has not yet developed Alzheimer's disease, whereby it can also be used as a method for preventing the development of Alzheimer's disease.

The term "β-amyloid" in the present embodiment refers to an amyloid protein, a peptide composed of 36 to 43 amino acids, which is cleaved from an amyloid β protein precursor (APP) by the action of β- and γ-secretases. In the present embodiment, β-amyloid preferably refers to a β-amyloid protein composed of 40 amino acids, a β-amyloid protein composed of 42 amino acids, and a β-amyloid protein composed of 43 amino acids, each of which may be abbreviated as $A\beta_{1-40}$, $A\beta_{1-42}$, or $A\beta_{1-43}$.

Specifically, the method for reducing a β-amyloid concentration in blood according to the present embodiment reduces a β-amyloid concentration in blood circulating the body by adsorption of $A\beta_{1-42}$ or $A\beta_{1-40}$ in blood to the hollow fiber membrane. According to the present embodiment, a method for reducing a β-amyloid concentration in blood circulating the body by adsorption of $A\beta_{1-43}$ to the hollow fiber membrane may also be provided.

In the present embodiment, the term "β-amyloid-albumin complex" refers to a complex formed by the electrostatic binding of β-amyloid to albumin. While β-amyloid can be present as free β-amyloid in blood, it is largely bound to albumin and present as a complex.

In the present embodiment, it is considered that β-amyloid is not adsorbed to the hollow fiber membrane in the form of a complex with albumin, but, as described in Examples, detached from the complex formed with albumin and directly adsorbed to the hollow fiber membrane.

Given that β-amyloid is a protein having a molecular weight of approximately 4 kDa, when artificial dialysis is performed as one aspect of the present embodiment by passing blood through a dialyzer, etc. containing a hollow fiber membrane, it was assumed to be filtered out and exuded into the dialysate side. However, studies conducted by the present inventors revealed that β-amyloid was not exuded into the dialysate side but removed by adsorption. The present inventors conducted an intensive study on the main mechanism of β-amyloid removal by a hollow fiber. As a result, we have found that even when a fluid containing β-amyloid is passed through the dialysate side, where normally a dialysate is passed through, i.e., at the outer surface of the hollow fiber of a dialyzer, while sealing the blood side of the dialyzer, where normally blood is passed through, β-amyloid still can be efficiently removed. We have also found that β-amyloid is still efficiently removed by contacting a fluid containing β-amyloid with macaroni-like hollow fibers that is finely cut. Based on the above observations, the present inventors have found that the main mechanism of β-amyloid removal by a hollow fiber is not filtration but adsorption.

In the present embodiment, the β-amyloid concentration in blood is reduced by adsorption of β-amyloid to the hollow fiber membrane. Here, the term "adsorption of β-amyloid to the hollow fiber membrane" refers to a state in which β-amyloid is electrostatically and/or hydrophobically bound to the surface of the hollow fiber membrane, and in this state, β-amyloid is considered to be detached from albumin.

When the hollow fiber membrane is a porous membrane with fine pores, β-amyloid may be physically caught in the fine pores; however, a majority of adsorbed β-amyloid is considered to be electrostatically and/or hydrophobically bound to the surface of the hollow fiber membrane.

In the present embodiment, when the blood of a patient is passed through the hollow fiber membrane, β-amyloid is detached from the β-amyloid-albumin complex, which is how it exists in blood, and adsorbed to the hollow fiber membrane. Meanwhile, albumin, the other component of the complex, is present in blood as a free form.

There is no particular limitation on the hollow fiber membrane used in the present embodiment as long as it can pass through the blood, and examples thereof include hollow fiber membranes used in artificial dialysis, blood filtration, plasma separation, and the like.

Examples of the hollow fiber membrane include a cellulose hollow fiber membrane such as cellulose acetate, modified cellulose, and cuprammonium cellulose, and a synthetic polymer hollow fiber membrane such as polyacrylonitrile, polymethylmethacrylate, polyethylene, polyvinylidene fluoride, polyethersulfone-polyarylate polymer alloy, polyvinyl alcohol, polysulfone, polyamide, polyimide, polyphenyl ether, polyether sulfone, and an ethylene vinyl alcohol copolymer. Among them, because electrostatic and/or hydrophobic binding is utilized, a hydrophobic polymer is preferably used, and a hollow fiber membrane formed by a polymer such as polysulfone, polymethylmethacrylate, polyethersulfone-polyarylate polymer alloy, polyether sulfone, and polyacrylonitrile is preferable.

Preferably, the material of the hollow fiber membrane is blood-compatible and further contains polyvinylpyrrolidone, polyethylene glycol, an ethylene vinyl alcohol copolymer, polyhydroxyethylmethacrylate, and the like. Examples of the hollow fiber membrane include one produced from a polymer mixture composed of polysulfone and polyvinylpyrrolidone.

Also, while the aforementioned polyvinylpyrrolidone and the like can be spun together with a polymer such as polysulfone, they can also be used to coat a hollow fiber membrane obtained by spinning with a polymer such as polysulfone. In the present embodiment, besides hollow fibers, porous threads and flat membranes can also be used as the hollow fiber membrane.

The hollow fiber membrane used in the present embodiment can be produced by a publicly known method.

As the membrane structure of the hollow fiber membrane, a straw-like hollow fiber membrane configured to have numerous coarse pores having a minor axis of 0.5 µm or more on the outer surface of the membrane is preferable. Also, the thickness of the hollow fiber membrane is preferably 0.01 to 1 mm.

In the present embodiment, the hollow fiber membrane is preferably used as a hollow fiber membrane-type module inserted in a housing.

There is no particular limitation on the form of the hollow fiber membrane in the housing as long as the hollow fiber membrane can contact the flowing blood; however, it may be attached inside the housing as a hollow fiber membrane or inserted in the housing as a fragment of the hollow fiber membrane.

When the hollow fiber membrane is contained in the housing, a bundle of hollow fiber membranes composed of numerous sticks of hollow fiber membranes can be inserted in a cylindrical housing as a hollow fiber membrane column-like hollow fiber membrane-type module.

In that case, both ends of the bundle of hollow fiber membranes may be sealed with a resin layer part, which serves as a sealing part formed by filling a resin composition such as polyurethane. Also, the housing preferably has an inlet port and an outlet port for the blood so that the blood passes through inside the housing and then be discharged therefrom.

Further, the housing may have an inlet port and an outlet port for a fluid so as to run a fluid through outside the hollow fiber membrane. When the hollow fiber membrane is used as a column that permits the blood to pass through inside the hollow fiber membrane, the inner cavity of the hollow fiber, which is an internal space of the hollow fiber, is separated from the space at the outer surface of the hollow fiber, and the blood passes through the inner cavity of the hollow fiber and then adsorbs to the surface of the inner cavity of the hollow fiber and a thick part of the hollow fiber (a porous part between the inner surface and the outer surface of the hollow fiber membrane). Also, when the hollow fiber membrane is used as a column that permits the blood to pass through the outer surface of the hollow fiber membrane, the blood passes through the outer surface of the hollow fiber and adsorbs to the outer surface of the hollow fiber and a thick part of the hollow fiber (a porous part between the inner surface and the outer surface).

Examples of the module having the hollow fiber membrane as described above include a module used as a so-called dialyzer (dialysis column) and the modules described in Japanese Patent Laid-Open No. 2005-52716, WO 2006/024902, WO 2004/094047, and the like, and these can be preferably used as the hollow fiber membrane of the present embodiment.

In the present embodiment, when the blood is contacted with the surface of the inner cavity of the hollow fiber using a hollow fiber membrane column, either gas or liquid may be present at the outer surface of the hollow fiber. The outer surface of the hollow fiber may be hermetically sealed, or when it is not sealed, the pressure at the outer surface of the hollow fiber is preferably pressure opened to the atmospheric pressure or lower than the blood pressure.

When gas or liquid is present at the outer surface of the hollow fiber, it may be present as a fluid body.

Examples of the gas include inert gas and air. Also, as the liquid, it is preferable to run through a solution used as a dialysate.

According to the method of the present embodiment, when the blood is passed through the inner cavity of the hollow fiber and the dialysate is passed through the outer surface of the hollow fiber, β-amyloid is substantially not exuded into the outer surface of the hollow fiber. Thus, the β-amyloid concentration in the dialysate is preferably substantially not increased.

In the present embodiment, when the blood is contacted with the outer surface of the hollow fiber using a hollow fiber membrane column, either gas or liquid may be present in the inner cavity of the hollow fiber. The inner cavity of the hollow fiber may be hermetically sealed, or when it is not sealed, the pressure in the inner cavity of the hollow fiber is preferably pressure opened to the atmospheric pressure or lower than the blood pressure.

Normally, when dialysis is performed, a concentration of low molecular weight compounds exuded into the dialysate side, etc. increases. However, in the present embodiment, the phrase "substantially not increased" refers to that such an increase in concentration is not observed. In the present embodiment, it refers to that β-amyloid is removed such that an amount of β-amyloid exuded into the dialysate side is equal to or less than 5%, preferably equal to or less than 1% of the amount of β-amyloid to be removed from the flowing blood.

Also, in that case, in order to increase the Aβ adsorption in the direction of thickness of the hollow fiber membrane (a part sandwiched between the outer surface and the inner surface of the hollow fiber), a configuration to be able to prevent positive filtration, and further, reverse filtration is preferable. To achieve such a configuration, for example, the filling ratio of the hollow fiber can be reduced or the hollow fiber can be made big and short in shape.

In the method for reducing a β-amyloid concentration in blood according to the present embodiment, the blood preferably contains β-amyloid-albumin complexes, in which β-amyloid is bound to albumin. The above method is performed as a method for reducing β-amyloid in blood, and the method includes the steps of removing the blood out of a body, passing the blood that is removed through a hollow fiber membrane having a hollow fiber membrane for dialysis in a housing having at least an inlet port and an outlet port, and returning the blood that is passed through into the body, wherein a flow rate of the blood outside the body is 5 to 200 mL/min, and the aforementioned step of passing through the blood permits β-amyloid to adsorb to the hollow fiber membrane and frees albumin from a β-amyloid-albumin complex, whereby reducing the β-amyloid concentration in blood.

According to the present embodiment, a β-amyloid removal system is also provided. The method for reducing a β-amyloid concentration in blood according to the present embodiment can be performed by the β-amyloid removal system.

The β-amyloid removal system according to the present embodiment includes;
a hollow fiber membrane that adsorbs β-amyloid and reduces the β-amyloid concentration in blood,
a blood circuit that removes the blood out of the body,
a blood circuit that returns the blood that is passed through the hollow fiber membrane, and
flexible tubes connecting the blood circuits to the hollow fiber membrane.

As the hollow fiber membrane of the β-amyloid removal system, the aforementioned hollow fiber membrane-type module can be used. The blood delivered through the blood-removal circuit is preferably passed through the inner cavity of the hollow fiber of the hollow fiber membrane-type module, and the flow rate of the blood is, as the flow rate of the blood contacting with the hollow fiber membrane, preferably 1 to 500 mL/min, more preferably 5 to 200 mL/min, and further, even more preferably 10 to 30 mL/min. In practical module designing, the removal rate of Aβ and the amount of blood treated per unit time need to be taken into consideration.

Also, time is required for β-amyloid to adsorb to the hollow fiber membrane. Thus, there is no particular limitation on the preferred embodiment of the linear velocity of the blood contacting with the hollow fiber membrane, and examples thereof in the cases in which the blood is passed through the inner cavity of the hollow fiber are given below.

For example, suppose there are approximately 10,000 hollow fibers per module, when the flow rate of the blood is 200 mL/min, the linear velocity of the blood in the inner cavity of the hollow fiber is approximately 64 cm/min in a hollow fiber having an inner diameter of 200 μm.

The linear velocity of the blood in the inner cavity of the hollow fiber is preferably 200 cm/min or less, more preferably 70 cm/min or less, even more preferably 10 cm/min or less, and still even more preferably 5 cm/min or less.

As a further specific example, the hollow fiber of the dialyzer used in Examples has an inner diameter of 200 μm and the volume of the inner cavity of the hollow fiber is 75 mL. Based on this, the retention time of the β-amyloid solution (equivalent to blood) in the hollow fiber is obtained as follows. When the flow rate of the blood is 200 mL/min (the removal rate of β-amyloid in the air-enclosed adsorption and passing-through experiment in Example 3 was 74.4%), the retention time is 0.4 minute, and the linear velocity of the blood in the inner cavity of the hollow fiber is 63.7 cm/min. When the flow rate of the blood is 50 mL/min (the removal rate of β-amyloid in the air-enclosed adsorption and passing-through experiment in Example 4 was 46.2%), the retention time is 1.5 minutes, and the linear velocity of the blood in the inner cavity of the hollow fiber is 15.0 cm/min. When the flow rate of the blood is 15 mL/min (the removal rate of β-amyloid in the air-enclosed adsorption and passing-through experiment in Example 5 was 94.5%), the retention time is 5 minutes, and the linear velocity of the blood in the inner cavity of the hollow fiber is 4.8 cm/min.

Meanwhile, from Table 6, it is found that a contact time of the blood and the hollow fiber membrane of five minutes is slightly insufficient for the removal of β-amyloid, and the adsorption of β-amyloid is almost completed in 15 minutes. That is, with the existing dialyzers (having an effective length of the hollow fiber in the adsorption area of approximately 24 cm), it is suggested that if the contact time of the hollow fiber membrane and Aβ can be set at approximately five minutes or longer, the removal rate of β-amyloid will be sufficiently high. When this is expressed as the linear velocity, it is 24 cm/5 minutes. That is, in a hollow fiber having an inner diameter of 200 μm, a linear velocity of approximately 5 cm/min or less is considered to be preferable.

It is to be noted that when the blood is passed through the outer surface of the hollow fiber, the blood may be passed through at a similar speed to the range of the preferred linear velocity.

As a device for maintenance of the aforementioned flow rate and linear velocity of the blood, the β-amyloid removal system may comprise a blood pump.

There is no particular limitation on the blood pump as long as it can continuously supply blood to the hollow fiber membrane, and examples thereof include pumps for a blood purification device and artificial dialysis, and a peristaltic pump (roller pump).

Also, normally, in the case when the blood is passed through a central membrane-type module and the like, an anticoagulant is added to the blood to prevent coagulation of the blood. Thus, a chamber where an anticoagulant is mixed with the blood may be provided.

Further, a pressure monitor for measuring the pressure of the flowing blood and a monitor for confirming bubbles in the returning blood may be provided. Also, the blood may be sampled.

Also, when the method for reducing a β-amyloid concentration in blood of the present embodiment is performed in accordance with blood filtration, a fluid replacement pump to supply a replacement fluid and a fluid replacement tank to store a replacement fluid, and the like may be provided.

In the β-amyloid removal system according to the present embodiment, β-amyloid is removed by adsorption to the surface of the hollow fiber membrane. Thus, in order also to increase the removal rate of β-amyloid, it is preferable to prevent reverse filtration, even partially, so that the blood can efficiently contact the inner cavity and inside the membrane thickness of the hollow fiber.

When a dialyzer-type hollow fiber membrane is used, reverse filtration can be prevented by setting the pressure at the dialysate side low. For this, there is no particular limitation on the flow rate in the dialysate side, it is preferably 100 mL/min or less.

Also, the surface of the hollow fiber in the opposite side to the blood side is preferably filled with gas. The gas at the surface of the hollow fiber in the opposite side to the blood side may be air, and openings of the fluid inlet and outlet ports for passing a liquid through the hollow fiber membrane side opposite to the blood side may be created so that the gas may be exposed to the atmosphere.

In that case, some of the plasma component of the flowing blood may be exuded into the surface of the hollow fiber opposite to the blood side; however, the exudation of the blood can be adjusted by appropriate monitoring.

In order to prevent reverse filtration when a dialysate is passed through the outer surface the hollow fiber, the flow rate of filtration from the blood side to the dialysate side is preferably controlled to a positive value of 0 mL/min or more.

The flow rate of filtration from the blood side to the dialysate side is preferably 5 mL/min or more, more preferably 12.5 mL/4 min or more.

Examples of a method for preventing reverse filtration as described above include keeping the filling rate of hollow fiber lower than the dialyzer for hemodialysis and keeping a ratio L/D, i.e., a ratio of length L to diameter D of the container containing an effective part of the hollow fiber lower than the dialyzer for hemodialysis, namely, making the container big and short.

Although a hollow fiber membrane-type module used as a dialyzer can be employed, fragments of the hollow fiber membrane may be inserted in the housing. In that case, while the thickness of the fragment of the hollow fiber membrane is approximately the same as the hollow fiber membrane before fragmentation, it is preferably 0.01 to 1 mm. The length of the hollow fiber membrane is preferably 0.2 to 200 mm, and more preferably 0.5 to 10 mm.

In the present embodiment, the fragment of the hollow fiber membrane can be obtained by cutting the spun hollow fiber membrane to a desired size.

EXAMPLES

Hereinbelow, the present embodiment will be further specifically described with reference to Examples and Comparative Examples; however, the present embodiment is not limited only to these Examples.

In the following Examples and Comparative Examples, as Aβ, hydrochloride salts of human $A\beta_{1-40}$ or human $A\beta_{1-42}$ manufactured by Wako pure chemical industries, Ltd. were used. The $A\beta_{1-40}$ or $A\beta_{1-42}$ was frozen as a 100 μg/mL solution of Aβ in dimethyl sulfoxide (DMSO), and this stock solution was thawed immediately before use.

<Example 1> Study Using a Hollow Fiber Mini Module (Adsorption and Passing-through Experiment)

Commercial dialyzers, i.e., a dialyzer made of polysulfone (PSf) (APS13E manufactured by Asahi Kasei Kuraray Medical CO., LTD., type IV: pore size large), a dialyzer made of modified cellulose (BEM) (AMBC-13F manufactured by Asahi Kasei Kuraray Medical CO., LTD., type II: pore size small), and a dialyzer made of an ethylene vinyl alcohol copolymer (EVAL) (kf-m12 manufactured by Asahi Kasei Kuraray Medical CO., LTD., type II: pore size small), were cut open with an ultrasonic cutter. Hollow fibers were taken out and washed with non-calcium-containing phosphate buffered saline (PBS) (pH 7.2), and then air dried.

Hollow fiber mini modules were created by firmly binding the end of a bundle of hollow fibers with polyethylene tubes and epoxy resin to produce a mount (corresponding to the header) so that the membrane area of the inner cavity of the hollow fiber was 65 cm$^2$ (approximately 1/200 of a product of 1.3 m$^2$) and an effective length of the hollow fiber was 10 cm, and using silicone tubes for connection.

Priming was then performed using a PERISTA pump (SJ-1211, manufactured by ATTO Corporation) by passing PBS through the hollow fiber mini module at a flow rate of 15 ml/hr (equivalent to 50 mL/min in a product of 1.3 m$^2$) for 20 minutes, and further, passing a 10 mg/ml solution of bovine serum albumin (BSA) (manufactured by Wako pure chemical industries, Ltd., without globulin, for biochemical use) in PBS through the hollow fiber mini module at a flow rate of 15 ml/hr (equivalent to 50 mL/min in a product of 1.3 m$^2$) for four minutes.

After priming, an $A\beta_{1-42}$/BSA/PBS solution, which was prepared by adding Aβ to a 10 mg/mL solution of BSA in PBS so that a concentration of 400 ng/mL (approximately 100 nM) was achieved (hereinbelow, may be abbreviated as a "400 ng/mL $A\beta_{1-42}$/BSA/PBS solution"), was passed through the hollow fiber mini module from A side (before hollow fiber mini module) to V side (after hollow fiber mini module) at a flow rate of 15 ml/hr (equivalent to 50 mL/min in a product of 1.3 m$^2$), and the Aβ solution discharged after passing through the hollow fiber mini module was collected zero (immediately after initiation of adsorption), one, and four hours after initiation of passing through the hollow fiber mini module.

Using Human β Amyloid (1-42) ELISA Kit, High-Sensitive (manufactured by Wako pure chemical industries, Ltd.), the $A\beta_{1-42}$ concentration in the collected sample solution was measured under conditions of a measurement wavelength of 450 nm and a reference wavelength of 620 nm by iMark Microplate Reader (manufactured by Bio-Rad Laboratories, Inc.). Subsequently, the removal rate of Aβ was obtained based on the following formula from a ratio of Aβ concentrations before and after the hollow fiber mini module.

$$\text{Removal rate of } A\beta = 100 \times \{1 - (A\beta \text{ concentration after hollow fiber mini module}/A\beta \text{ concentration before hollow fiber mini module})\} \quad \text{Formula:}$$

The results thus obtained are shown in Table 1. Over four hours, nearly all of the Aβ in the flowing solution was found to be removed irrespective of the material and the pore size. Table 1: The removal rate of Aβ by a hollow fiber mini module (adsorption and passing-through experiment)

TABLE 1

| Removal rate of Aβ (%) | 0 h | 1 h | 4 h |
|---|---|---|---|
| PSf | 97.2 | 97.4 | 85.4 |
| BEM | 97.9 | 97.8 | 91.8 |
|  | 97.9 | 97.5 | 90.5 |
| EVAL | 97.6 | 97.6 | 88.6 |
|  | 97.2 | 97.4 | 90.2 |

<Experiment 2> Study Using a Hollow Fiber Mini Module (Complete Filtering)

Similarly to Example 1, using a hollow fiber mini module and a PERISTA pump, priming was performed by passing PBS at a flow rate of 15 ml/hr (equivalent to 50 mL/min in a product of 1.3 m$^2$) for 20 minutes, and further, passing a 10 mg/ml solution of bovine serum albumin (BSA) (manufactured by Wako pure chemical industries, Ltd., without globulin, for biochemical use) in PBS at a flow rate of 15 ml/hr (equivalent to 50 mL/min in a product of 1.3 m$^2$) for four minutes.

After priming, the V side of the hollow fiber mini module was completely closed, and a 400 ng/mL A$\beta_{1-42}$/BSA/PBS solution was passed from A side (before the hollow fiber mini module) to V side (after the hollow fiber mini module) at a flow rate of 15 ml/hr, and the A$\beta$ solution filtrated through the hollow fiber mini module and dripping down from the outer surface thereof was collected zero (immediately after initiation of complete filtering), 30, and 60 minutes after the A$\beta$ solution reached the entire hollow fiber mini module and complete filtering was started.

The A$\beta_{1-42}$ concentration in the sample solution thus collected was measured similarly to Example 1 to obtain the removal rate of A$\beta$.

The results thus obtained are shown in Table 2. With EVAL and BEM having a small pore size, a certain amount of A$\beta$ was exuded into the filtrate, whereas with PSf having a large pore size, the A$\beta$ concentration in the filtrate was almost undetectable immediately after initiation of complete filtering but then increased along with the progression of the filtration (a pressure rise).

From the results of Examples 1 and 2, adsorption was presumed to be the main mechanism of β-amyloid removal.

TABLE 2

The removal rate of A$\beta$ by a hollow fiber mini module (complete filtering)

| Removal rate of A$\beta$ (%) | 0 h | 1 h | 4 h |
| --- | --- | --- | --- |
| PSf | 99.8 | 62.1 | 60.5 |
|  | 99.8 | 67.4 | 57.8 |
| BEM | 87.5 | 72.2 | 49.0 |
| EVAL | 69.4 | 70.9 | Stopped due to a pressure rise |
|  | 89.0 | 53.0 | Stopped due to a pressure rise |

<Example 3> Study Using a Dialyzer (Adsorption and Passing-through Experiment)

An experimental circuit was constructed with a commercial dialyzer, a dialyzer manufactured by Asahi Kasei Kuraray Medical CO., LTD. (APS13S), and a dialysis blood circuit (AP-53B manufactured by Gambro), using a slow extended hemopurification device (ACH-10 manufactured by Asahi Kasei Kuraray Medical CO., LTD.).

Both the blood and dialysate sides of the dialyzer were primed with 500 ml of PBS at a flow rate of 200 ml/min. Then, only the blood side was passed to prime with a 5 mg/ml BSA/PBS solution at a flow rate of 200 ml/min for 30 minutes.

After draining the fluid retained in the dialysate side, both ports on the A and D sides were plugged, and the dialysate side was completely closed with air enclosed inside. Then, the BSA/PBS solution which had filled the line at priming was replaced with 200 mL of a 4 ng/mL A$\beta_{1-40}$/BSA/PBS solution, which was prepared by adding A$\beta$ to a 5 mg/mL BSA/PBS solution so that a concentration of 4 ng/mL A$\beta_{1-40}$ was achieved, from the A side (before the blood circuit dialyzer). Subsequently, the 4 ng/mL A$\beta_{1-40}$/BSA/PBS solution was passed through the dialyzer from the A side to the V side (after the blood circuit dialyzer) for four minutes at a flow rate of 200 mL/min. The A$\beta_{1-40}$ solutions immediately before initiation of the experiment, before and after the dialyzer four minutes after initiation were sampled. Further, a small amount of solution leaking out into the dialysate side (D side) was collected and a solution discharged from the outlet port on V side after passing through the dialyzer was collected for four minutes. Each of the above solutions was stirred to homogeneity, and a portion was taken from each solution to serve as a sample solution. In this case, the linear velocity of the blood in the inner cavity of the hollow fiber was 63.7 cm/min.

Using Human β Amyloid (1-40) ELISA Kit II (manufactured by Wako pure chemical industries, Ltd.), the A$\beta_{1-40}$ concentration in the collected sample solution was measured under conditions of a measurement wavelength of 450 nm and a reference wavelength of 620 nm by iMark Microplate Reader (manufactured by Bio-Rad Laboratories, Inc.).

Subsequently, the absolute amount of the input A$\beta$ was obtained from a product of the amount of fluid infused into the dialyzer and the A$\beta$ concentration, and the absolute amount of the output A$\beta$ was obtained from a product of the amount of fluid discharged from the V and D sides and the A$\beta$ concentration. Then, the removal rate of A$\beta$ was obtained from the absolute amount as follows; Removal rate of A$\beta$=100×{1−(absolute amount of A$\beta$ discharged from V side of dialyzer)/(absolute amount of A$\beta$ infused into A side of dialyzer)}, and the leakage rate of A$\beta$ into the D side was obtained from the absolute amount as follows;

Leakage rate of $A\beta = 100 \times \{1-(\text{absolute amount of } A\beta \text{ discharged from } D \text{ side of dialyzer})/(\text{absolute amount of } A\beta \text{ infused into } A \text{ side of dialyzer})\}$.

The results thus obtained are shown in Table 3.

<Example 4> Study Using a Dialyzer (Adsorption and Passing-through Experiment)

Except for changing the flow rate of the 4 ng/mL A$\beta_{1-40}$/BSA/PBS solution to 50 mL/min, an adsorption and permeation experiment was performed in the same manner as Example 3. In this case, the linear velocity of the blood in the inner cavity of the hollow fiber was 15.0 cm/min. The results thus obtained are shown in Table 3.

<Example 5> Study Using a Dialyzer (Adsorption and Passing-through Experiment)

Except for changing the flow rate of the 4 ng/mL A$\beta_{1-40}$/BSA/PBS solution to 15 mL/min, an adsorption and permeation experiment was performed in the same manner as Example 3. In this case, the linear velocity of the blood in the inner cavity of the hollow fiber was 4.8 cm/min. The results thus obtained are shown in Table 3.

<Example 6> Study Using a Dialyzer (Adsorption and Passing-through Experiment)

Except for enclosing a fluid (purified water) in the dialysate side, an adsorption and permeation experiment was performed in the same manner as Example 3. The results thus obtained are shown in Table 3.

<Example 7> Study Using a Dialyzer (Adsorption and Passing-through Experiment)

After priming similarly to Example 3, the fluid retained in the blood side was drained. Then, both ports on the A and V sides were plugged, and the blood side (inner cavity of the hollow fiber) was completely closed with air enclosed inside. Then, the BSA/PBS solution which had filled the dialysate side (outer surface of the hollow fiber) at priming was replaced with 200 mL of a 4 ng/mL $A\beta_{1-40}$/BSA/PBS solution from the D-port inlet. Subsequently, the 4 ng/mL $A\beta_{1-40}$/BSA/PBS solution was passed through the dialyzer from the D-port inlet to the D-port outlet at the dialysate side for four minutes at a flow rate of 200 mL/min to carry out an adsorption and permeation experiment on the outer surface of the hollow fiber. The results thus obtained are shown in Table 3.

Table 3: The removal rate of $A\beta$ by a dialyzer (adsorption and passing-through experiment)

TABLE 3

| $A\beta$ solution-contacting side | Enclosed substance at the opposite side of $A\beta$ solution | Qb (ml/min) | Removal rate of $A\beta$ (from absolute amount) (%) | Rate of filtration leakage from hollow fiber (%) |
|---|---|---|---|---|
| Adsorption and permeation experiment | Inside hollow fiber | Air | 200 | 74.4 | 0.003 |
| | | | 50 | 46.2 | 0 |
| | | | 15 | 94.5 | 0 |
| | | Liquid (purified water) | 200 | 32.9 | 0.2 |
| | Outside hollow fiber | Air | | 68.6 | n.d. |

<Example 8> Study Using a Dialyzer (Dialysis Experiment)

Upon completion of the adsorption and passing-through experiment of Example 3, the blood circuits before and after the dialyzer were closed, and the circuit at the dialysate side was washed with PBS at a flow rate of 80 mL/min for five minutes (a total of 400 mL). Subsequently, 200 mL of PBS was circulated in the dialysate side of the dialyzer as a pseudo-dialysate at a dialysate-side flow rate (QD) of 83 mL/min for four minutes (this dialysate flow rate is one-sixth of the normal hemodialysis performed in a dialysis patient). During this time, a 4 ng/mL $A\beta_{1-40}$ solution was passed through the dialyzer from the A side to the V side at a blood-side flow rate (QB) of 200 mL/min for four minutes.

The $A\beta_{1-40}$ solutions immediately before initiation of the experiment, and the one before and after the dialyzer four minutes after initiation were sampled, and further, PBS used as the dialysate and a solution discharged from the outlet port at the V side after passing through the dialyzer that was collected for four minutes were each stirred to homogeneity, and a portion was taken from each solution to serve as a sample solution. Then, the removal rate of $A\beta$ was obtained by the same calculation formula as Example 3. The results thus obtained are shown in Table 4.

<Example 9> Study Using a Dialyzer (Dialysis Experiment)

Except for using a large roller pump and changing the flow rate in the dialysate side to 500 mL/min, a dialysis experiment was performed in the same manner as Example 8.

The results thus obtained are shown in Table 4. The results of Example 6, in which the flow rate in the dialysate side was set at 0 ml/min (i.e., the fluid was enclosed), are also shown in Table 4.

Table 4: The removal rate of $A\beta$ by a dialyzer (dialysis experiment)

TABLE 4

| $A\beta$ solution-contacting side | Flow rate of $A\beta$ solution Qb (ml/min) | Dialysate-side flow rate Qd (ml/min) | Removal rate of $A\beta$ (from absolute amount) (%) | Rate of filtration leakage from hollow fiber (%) |
|---|---|---|---|---|
| Dialysis experiment | Inside hollow fiber | 200 | 0 (Enclosed) | 32.9 | 0.2 |
| | | | 83.3 | 74.4 | 0.003 |
| | | | 500 | 68.6 | 0 |

<Example 10> Study Using a Dialyzer (Complete Filtering Experiment)

Upon completion of the dialysis experiment of Example 8, the blood circuit before and after the dialyzer was closed and the fluid retained in the dialysate side was drained. Subsequently, the blood circuit before the dialyzer was opened, while the upper port of the dialysate side was closed. Subsequently, the V side was closed, and a 4 ng/mL $A\beta_{1-40}$ solution was passed through at a flow rate of 200 ml/min for four minutes from the A side in the direction of membrane thickness of the dialyzer. The $A\beta_{1-40}$ solution immediately before initiation of the experiment and a filtrated solution discharged from the lower port of the dialysis side that was collected for four minutes were each stirred to homogeneity, and a portion was taken from each solution to serve as a sample solution. Then, the removal rate of $A\beta$ was obtained by the same calculation formula as Example 3. The results thus obtained are shown in Table 5.

Table 5: The removal rate of $A\beta$ by a dialyzer (complete filtering experiment)

TABLE 5

| $A\beta$ solution-contacting side | Flow rate of $A\beta$ solution Qb (ml/min) | Removal rate of $A\beta$ (from absolute amount) (%) | Rate of filtration leakage from hollow fiber (%) |
|---|---|---|---|
| Complete filtering experiment | Inside hollow fiber | 200 | 99.9 | 0.1 |

In the dialysis experiment, the removal rate of $A\beta$ was around 70%, indicating that almost no $A\beta$ transferred to the dialysate side. Further, in the complete filtering experiment also, only 0.1% of $A\beta$ was shown to have transferred to the filtrate. From this, it is considered that $A\beta$ was removed by adsorption to the hollow fiber membrane in the dialyzer.

Although an Aβ monomer is a small molecule with a molecular weight of approximately 4 kDa, the results of the dialysis experiment and the complete filtering experiment showed that a very small amount of Aβ transferred from inside to outside the hollow fiber, indicating that the adsorption to the hollow fiber membrane was the main mechanism of Aβ removal.

<Example 11> Study Using Fragments of the Hollow Fiber

A commercial dialyzer made of polysulfone (APS-15SA manufactured by Asahi Kasei Kuraray Medical CO., LTD.) was cut open with an ultrasonic cutter. Hollow fibers were taken out and washed well with PBS, and then air dried.

Then, 350 dried hollow fibers that were cut into 19-cm length pieces were fragmented into 1 cm-length pieces and packed into a 15-mL centrifugation tube made of PP. To this, 10 mL of an $A\beta_{1-40}$/BSA/PBS solution adjusted to 40 ng/mL with a 10 mg/mL BSA/PBS solution was added, and while shaking, the solution was sampled after 15, 30, and 60 minutes, and four and 16 hours, and the removal rate of Aβ was obtained from a ratio of $A\beta_{1-40}$ concentration to control. As a control, an $A\beta_{1-40}$/BSA/PBS solution in a centrifugation tube made of PP was prepared without adding fragments of the hollow fiber membrane, and then similarly shaken, and the solution sampled after 15, 30, and 60 minutes, and four and 16 hours was used.

With respect also to the cases in which six, 60, and 240 hollow fibers were used, the solution was similarly sampled after 5, 15, 30, and 60 minutes, and four hours, in which the removal rate of Aβ was measured.

The surface area of the inner cavity of the hollow fiber was as follows; 418 cm² for 350 hollow fibers, 286 cm² for 240 hollow fibers, 71.4 cm² for 60 hollow fibers, and 7.1 cm² for six hollow fibers. The results of measurement are shown in Table 6.

Table 6: The removal rate of Aβ by fragments of the hollow fiber membrane

TABLE 6

| min | 350 pieces | 240 pieces | 60 pieces | 6 pieces |
|---|---|---|---|---|
| 5 | n.d. | 83.8 | 65.0 | 42.8 |
| 15 | 97.0 | 94.8 | 81.4 | 39.7 |
| 30 | 97.5 | 98.0 | 85.7 | 39.7 |
| 60 | 98.4 | 99.1 | 89.5 | 39.0 |
| 240 | 99.0 | 99.4 | 86.0 | 40.6 |
| 960 | 98.6 | n.d. | n.d. | n.d. |

<Example 12> Study on the Removal Rate of Aβ Depending on a Ratio of Aβ to Albumin (Priming Only with PBS)

A commercial dialyzer made of polysulfone (APS-15SA manufactured by Asahi Kasei Kuraray Medical CO., LTD.) was cut open with an ultrasonic cutter. Hollow fibers were taken out and washed well with PBS, and then air dried.

Then, 350 dried hollow fibers that were cut into 19-cm length pieces were fragmented into 1 cm-length pieces and packed into a 15-mL centrifugation tube made of polypropylene (PP). Then, after priming with non-BSA-containing PBS for 15 minutes, the priming solution was drained. Subsequently, 10 mL of a 4 ng/mL $A\beta_{1-40}$/BSA/PBS solution, which was prepared by adding Aβ to PBS with various concentrations of BSA, was added, and while shaking, the solution was sampled after 15 and 30 minutes. The $A\beta_{1-40}$ concentration was measured in a similar manner to Example 11.

While the nominal $A\beta_{1-40}$ concentration was kept constant at 4 ng/mL, five levels of molar ratios of Aβ:BSA were used, which were; 1:74000 (5 mg/mL BSA), 1:10, 1:1, 1:0.1, and 1:0 (no BSA). The removal rate of Aβ was obtained from a ratio of the concentration of remaining Aβ in the presence of the fragment of hollow fiber membrane to the Aβ concentration in the control (without the fragment of hollow fiber membrane) under the same conditions and at the same time. The results thus obtained are shown in Table 7.

Table 7: Difference in the removal of Aβ depending on a molar ratio of $A\beta_{1-40}$ to albumin (priming only with PBS)

TABLE 7

| | | 15 min | | 30 min | |
|---|---|---|---|---|---|
| non Alb-priming | Aβ:BSA | $A\beta_{1-40}$ concentration | Removal rate | $A\beta_{1-40}$ concentration | Removal rate |
| With fragment of hollow fiber | 1:74000 | 0 | 100% | 12.4 | 99.2% |
| | 1:10 | 0 | 100% | 14 | 98.0% |
| | 1:1 | 0 | 100% | 9.3 | 95.7% |
| | 1:0.1 | 9.3 | * | 0 | * |
| | 1:0 | 1.6 | 97.7% | 0 | 100% |
| Without fragment of hollow fiber | 1:74000 | 1478.3 | | 1528.8 | |
| | 1:10 | 803.2 | | 714.0 | |
| | 1:1 | 166.8 | | 217.3 | |
| | 1:0.1 | 0 | | 0 | |
| | 1:0 | 69.8 | | 31.0 | |

<Example 13> Study on the Removal Rate of Aβ Depending on a Ratio of Aβ to Albumin (in the Case of Priming with Albumin-containing PBS)

Except for changing the priming solution to 5 mg/mL BSA-containing PBS, the $A\beta_{1-40}$ concentration was measured to obtain the removal rate of Aβ in the same manner as Example 12. The results thus obtained are shown in Table 8.

Table 8: Difference in the removal of Aβ depending on a molar ratio of $A\beta_{1-40}$ to albumin (priming with albumin-containing PBS)

TABLE 8

| Alb-priming | Aβ:BSA | 15 min Aβ$_{1-40}$ concentration | Removal rate | 30 min Aβ$_{1-40}$ concentration | Removal rate |
|---|---|---|---|---|---|
| With fragment of hollow fiber | 1:74000 | 24.8 | 97.7% | 4.7 | 99.5% |
| | 1:10 | 24.8 | 96.6% | 1.6 | 99.8% |
| | 1:1 | 34.1 | 78.6% | 15.5 | 95.6% |
| | 1:0.1 | 1.6 | * | 9.3 | 80.0% |
| | 1:0 | 0 | * | 18.6 | 4.1% |
| Without fragment of hollow fiber | 1:74000 | 1086.4 | | 1032.1 | |
| | 1:10 | 729.5 | | 725.6 | |
| | 1:1 | 159.1 | | 349.2 | |
| | 1:0.1 | 0 | | 46.6 | |
| | 1:0 | 0 | | 19.4 | |

Whether the removal of Aβ by hollow fibers in Examples 12 and 13 was studied by adsorption and filtration of Aβ-albumin complexes or adsorption of Aβ dissociated from Aβ-albumin complexes was studied.

Because Aβ adsorbs also to the tube wall of a centrifugation tube made of PP, the Aβ concentration decreases even when the fragment of hollow fiber is absent. Because the Aβ concentrations at 15 minutes and 30 minutes were almost equal, the adsorption of Aβ to the tube wall has already been completed at 15 minutes.

In Example 12, when the fragment of the hollow fiber was present, irrespective of the molar ratio of Aβ:BSA, the concentration of remaining Aβ became almost zero (approximately 1% or less than 1% of a nominal concentration of 4000 pg/mL) as a result of a 15-minute contact. From this, it is considered that Aβ dissociated from Aβ-albumin complexes was adsorbed to the hollow fiber membrane. Accordingly, it is considered that there are numerous adsorption sites for Aβ in addition to adsorption sites for albumin on the surface of the hollow fiber membrane, enabling efficient removal of Aβ dissociated from Aβ-albumin complexes.

Also, the actual blood contains a large amount of albumin, i.e., as much as 50 mg/mL. In Example 13, despite priming with a high concentration of albumin (BSA) to mimic the actual blood, the removal of Aβ by the hollow fiber was only slightly inhibited. Also, similarly to Example 12, irrespective of the molar ratio of Aβ:BSA, Aβ was efficiently removed as the concentration of remaining Aβ decreased to approximately 1% or less than 1% of a nominal concentration of 4000 pg/mL as a result of a 15-minute contact. In this experiment also, Aβ was efficiently adsorbed without being affected much by albumin coating applied in advance (priming with albumin-containing PBS). Thus, it was suggested that there were numerous adsorption sites for Aβ in addition to adsorption sites for albumin on the surface of the hollow fiber membrane, enabling efficient removal of Aβ dissociated from Aβ-albumin complexes.

On the other hand, with regard to the concentration of remaining Aβ$_{1-40}$ in the absence of the hollow fiber, even when priming was performed with albumin-containing PBS in Example 13, it also decreased in a manner dependent on the ratio of albumin:Aβ similarly to Example 12 in which priming was performed with non-albumin-containing PBS. This indicates that, even when the adsorption site on the PP tube wall is blocked in advance by priming with albumin, the adsorption rate of Aβ$_{1-40}$ changes depending of the magnitude of the molar ratio of albumin:Aβ, similarly to Example 12 (priming with non-albumin-containing PBS). Namely, this indicates that, irrespective of the remaining number of the adsorption site for albumin on the PP tube wall, albumin in the solution binds to Aβ, preventing Aβ from adsorbing to the PP tube wall (i.e., albumin in the solution draws Aβ available for adsorption to the PP tube wall into the solution side). In other words, it can be said that the adsorption of Aβ to the PP tube wall is inhibited due to formation of Aβ-albumin complexes in the solution. Accordingly, when the fragment of the hollow fiber is present, even when the molar ratio of albumin:Aβ in the solution is high (i.e., the albumin concentration is high) and Aβ-albumin complexes are formed, the removal rate of Aβ is as high as approximately 98%. That is, the fragment of the hollow fiber is considered to have an ability to detach Aβ from the complex to adsorb it.

<Example 14> Study Using Fragments of the Hollow Fiber Membrane (In Vitro)

Three commercial dialyzers: a dialyzer made of polysulfone (PSf) (APS-15SA manufactured by Asahi Kasei Kuraray Medical CO., LTD.), a dialyzer made of polymethylmethacrylate (PMMA) (BG-1.3PQ manufactured by Toray Medical Co., Ltd.), and a dialyzer made of cellulose triacetate (CTA) (FB-150Uβ manufactured by Nipro Corporation), were each cut open with an ultrasonic cutter. Hollow fibers were taken out and washed with PBS, and then air dried. The spacer yarn contained in the dialyzer made of PMMA was removed by tweezers.

Two hundred and forty dried hollow fibers that were cut into 19-cm length pieces were fragmented into 1 cm-length pieces and packed into a 15-mL centrifugation tube made of PP.

Then, 10 mL of an Aβ$_{1-42}$/BSA/PBS solution adjusted to 40 ng/mL with a 10 mg/ml BSA solution was added, and while shaking, the solution was sampled after 30 minutes, and one, two, and four hours.

Using High-Sensitive ELISA for Aβ$_{1-42}$ (Wako pure chemical industries, Ltd.), the Aβ$_{1-42}$ concentration was measured. The removal rate of Aβ was obtained from a ratio of the Aβ$_{1-42}$ concentration to control. As a control, an Aβ$_{1-40}$/BSA/PBS solution in a centrifugation tube made of PP was prepared without adding fragments of the hollow fiber membrane and then similarly shaken, and the solution sampled after 30 minutes and one, two, and four hours was used. The results thus obtained are shown in Table 9.

Table 9: The removal rate of Aβ depending on the fragment of hollow fiber membrane

TABLE 9

| | 30 min | | | 1 h | | | 2 h | | | 4 h | | |
|---|---|---|---|---|---|---|---|---|---|---|---|---|
| PSf average rate (%) | 92.8 | 97.8 / 96.4 | 98.5 | 95.6 | 98.5 / 97.7 | 98.9 | 97.3 | 99.1 / 98.5 | 99.0 | 98.0 | 99.4 / 98.9 | 99.4 |
| PMMA average rate (%) | 86.2 | 91.4 / 90.5 | 94.0 | 94.8 | 91.5 / 93.9 | 95.5 | 95.2 | 96.4 / 96.2 | 96.8 | 96.0 | 96.8 / 96.8 | 97.6 |
| CTA average rate (%) | 73.4 | 72.5 / 72.3 | 70.9 | 76.0 | 73.0 / 72.6 | 68.9 | 73.2 | 73.5 / 72.5 | 70.6 | 73.1 | 73.2 / 72.2 | 70.2 |

<Example 15> Study Using a Dialyzer (In Vivo)

A group of dialysis patients consisted of 37 non-diabetic patients, 16 males and 21 females, at the age of 59 to 75 (mean 68.9±4.1) years with a dialysis vintage of 2 to 35 (mean 11.5±8.0) years. A four-hour dialysis was continued three times a week at a blood flow rate of 200 mL/min and a dialysate flow rate of 400 to 500 mL/min. As an anticoagulant, heparin was used.

Thirty one patients were on a dialyzer made of polysulfone (PSf) (APS-15SA, APS-18SA, APS-21SA, and APS-18MD manufactured by Asahi Kasei Kuraray Medical CO., LTD.), three patients were on a dialyzer made of cellulose triacetate (CTA) (FB-150Uβ manufactured by Nipro Corporation), two patients were on a dialyzer made of polymethylmethacrylate (PMMA) (BG-1.3PQ manufactured by Toray Medical Co., Ltd.), and two patients were on a dialyzer made of polyethersulfone-polyarylate polymer alloy (PEPA) coated with polyvinylpyrrolidone (FDY-210GW manufactured by Nikkiso Co., Ltd.). One patient was measured twice in total using dialyzers made of different materials.

One hour after initiation of dialysis, samples were collected from the blood circuit at the inlet and outlet ports of the dialyzer and the removal rate of Aβ before and after the column by the dialyzer was obtained.

For each material of the hollow fiber, a mean value of the removal rate of $A\beta_{1-40}$ before and after the dialyzer one hour after initiation of dialysis was as follows; 68.9% for polysulfone, 51.4% for CTA, 60.8% for PMMA, and 60.7% for PEPA, while a mean value of the removal rate of $A\beta_{1-42}$ before and after the dialyzer one hour after initiation of dialysis was as follows; 53.5% for polysulfone, 40.0% for CTA, 48.6% for PMMA, and 42.7% for PEPA.

The invention claimed is:

1. A method for reducing β-amyloid concentration in blood of a patient diagnosed with Alzheimer's disease or with accumulation of β-amyloid in the brain, comprising:
   removing blood out of a body of the patient,
   passing the removed blood through a hollow fiber membrane comprising at least one polymer to obtain a filtrate,
   allowing β-amyloid contained in the blood to adsorb directly to the at least one polymer of the hollow fiber membrane by at least one of electrostatic and hydrophobic interaction between the β-amyloid and the at least one polymer of the hollow fiber membrane, so that the β-amyloid concentration in blood is reduced by the direct adsorption of the β-amyloid to the hollow fiber membrane due to the electrostatic and/or hydrophobic interaction between the β-amyloid and the at least one polymer of the hollow fiber membrane; and
   returning the blood that is passed through with or without the obtained filtrate into the body of the patient,
   wherein:
   the at least one polymer is selected from the group consisting of polysulfone (PSf), polymethylmethacrylate (PMMA), polyethersulfone-polyarylate polymer alloy (PEPA), polyethersulfone (PES), and polyacrylonitrile (PAN),
   the blood is passed through an inner cavity or an outer cavity of the hollow fiber membrane;
   gas or liquid is present at an opposite side of the hollow fiber membrane to the blood side;
   a removal rate of β-amyloid from the removed blood is greater than 42.7%; and
   at least 95% of the β-amyloid removed from the patient's blood is directly adsorbed to the at least one polymer of the hollow fiber membrane.

2. The method according to claim 1, wherein β-amyloid from a β-amyloid-albumin complex adsorbs directly to the at least one polymer and albumin from the β-amyloid-albumin complex is liberated into the blood.

3. The method according to claim 1, wherein a flow rate of the blood is 5 to 200 mL/min.

4. The method according to claim 1, wherein a flow rate of the blood is 10 to 50 mL/min.

5. The method according to claim 1, wherein the blood is passed through an inner cavity of the hollow fiber.

6. The method according to claim 5, wherein a linear velocity of the blood in the inner cavity of the hollow fiber is 200 cm/min or less.

7. The method according to claim 5, wherein a linear velocity of the blood in the inner cavity of the hollow fiber is 5 cm/min or less.

8. The method according to claim 5, wherein the gas or liquid is present at an outer surface of the hollow fiber and a flow rate of the gas or liquid is 0 ml/min.

9. The method according to claim 1, wherein a dialysate is passed through an outer surface of the hollow fiber.

10. The method according to claim 9, wherein a β-amyloid concentration in the dialysate is substantially not increased.

11. The method according to claim 1, wherein the blood is passed through an outer surface of the hollow fiber.

12. The method according to claim 11, wherein the gas or liquid is present in the inner cavity of the hollow fiber and a flow rate of the gas or liquid is 0 ml/min.

13. The method according to claim 1, wherein the hollow fiber membrane is positioned in a housing having an inlet port and an outlet port for the blood.

14. The method according to claim 13, wherein the hollow fiber membrane is positioned in the housing and sealed at the inlet port and the outlet port.

15. The method according to claim 14, wherein the housing of the hollow fiber membrane is a hemodialysis column.

16. The method according to claim 13, wherein a fragment of the hollow fiber membrane is positioned in the housing.

17. The method according to claim 1, wherein:
the removed blood contacts the inner surface of the hollow fiber membrane for at least about 0.4 minutes, and
the outer surface of the hollow fiber membrane is in contact with the gas or liquid, which has a flow rate of 0 ml/min.

18. The method according to claim 1, wherein the removal rate of β-amyloid from the blood of the patient is greater than 68.9%.

19. The method according to claim 1, wherein the removal rate of β-amyloid from the blood of the patient is greater than 85.4%.

20. The method according to claim 1, wherein the removal rate of β-amyloid from the blood of the patient is greater than 97.9%.

21. The method for reducing a β-amyloid concentration in blood according to claim 1, wherein the at least one polymer is polysulfone (PSf).

22. The method for reducing a β-amyloid concentration in blood according to claim 1, wherein the at least one polymer is polymethylmethacrylate (PMMA).

23. The method for reducing a β-amyloid concentration in blood according to claim 1, wherein the at least one polymer is polyethersulfone-polyarylate polymer alloy (PEPA).

24. The method for reducing a β-amyloid concentration in blood according to claim 1, wherein the at least one polymer is polyethersulfone (PES).

25. The method for reducing a β-amyloid concentration in blood according to claim 1, wherein the at least one polymer is polyacrylonitrile (PAN).

* * * * *